(12) United States Patent
Lyon et al.

(10) Patent No.: US 12,144,118 B2
(45) Date of Patent: Nov. 12, 2024

(54) EMBEDDED SYSTEM MODULE THERMAL INSTALLATION VERIFICATION

(71) Applicant: L3Harris Technologies, Inc., Melbourne, FL (US)

(72) Inventors: Craig K. Lyon, West Jordan, UT (US); Craig R. Parker, Centerville, UT (US); Christopher D. Jensen, Morgan, UT (US); Preston Balfour, South Jordan, UT (US)

(73) Assignee: L3Harris Technologies, Inc., Melbourne, FL (US)

( * ) Notice: Subject to any disclaimer, the term of this patent is extended or adjusted under 35 U.S.C. 154(b) by 500 days.

(21) Appl. No.: 17/495,448

(22) Filed: Oct. 6, 2021

(65) Prior Publication Data

US 2023/0108232 A1  Apr. 6, 2023

(51) Int. Cl.
*H05K 13/08* (2006.01)
*H01L 23/34* (2006.01)
*H05K 7/20* (2006.01)

(52) U.S. Cl.
CPC .......... *H05K 13/083* (2018.08); *H01L 23/34* (2013.01); *H05K 7/20* (2013.01); *H05K 7/2039* (2013.01); *H05K 2201/06* (2013.01); *H05K 2201/066* (2013.01); *H05K 2203/16* (2013.01)

(58) Field of Classification Search
CPC .............. H05K 7/207; H05K 2203/16; H05K 2201/06; H05K 2201/066; H05K 13/083; H05K 7/20; H05K 7/2039; H01L 23/34
See application file for complete search history.

(56) References Cited

U.S. PATENT DOCUMENTS

2007/0140030 A1* 6/2007 Wyatt ................. G11C 5/00
 365/212
2008/0040067 A1* 2/2008 Bashor ................ G06F 11/24
 714/E11.154
2020/0225719 A1* 7/2020 Scott, III ........... G06F 11/3037

* cited by examiner

*Primary Examiner* — Jennifer Bahls
(74) *Attorney, Agent, or Firm* — Workman Nydegger

(57) ABSTRACT

Systems and methods for detecting an incorrectly attached heat sink component on an electronic device. The system includes one or more temperature sensors secured to the electronic device and a controller unit comprising one or more processors and one or more computer-readable media, the computer-readable media having stored thereon executable instructions that are executable by the one or more processors to perform a method for detecting incorrectly attached heat sink components. The method includes receiving temperature data, calculating a thermal ramp rate, comparing the thermal ramp rate to a predetermined threshold ramp rate, and transmitting a fault signal when the calculated thermal ramp rate exceeds the predetermined threshold ramp rate.

20 Claims, 8 Drawing Sheets

FIG. 5

| Power (W) | Ambient Temperature (°C) | | | | | | | | | | | | | | | | | | | | | | | | |
|---|---|---|---|---|---|---|---|---|---|---|---|---|---|---|---|---|---|---|---|---|---|---|---|---|---|
| | 75.00 | 70.00 | 65.00 | 60.00 | 55.00 | 50.00 | 45.00 | 40.00 | 35.00 | 30.00 | 25.00 | 20.00 | 15.00 | 10.00 | 5.00 | 0.00 | -5.00 | -10.00 | -15.00 | -20.00 | -25.00 | -30.00 | -35.00 | -40.00 |
| 85.00 | 1.600 | 1.586 | 1.572 | 1.558 | 1.544 | 1.530 | 1.516 | 1.502 | 1.488 | 1.474 | 1.460 | 1.446 | 1.432 | 1.418 | 1.404 | 1.390 | 1.376 | 1.362 | 1.348 | 1.334 | 1.320 | 1.306 | 1.292 | 1.278 |
| 81.46 | 1.565 | 1.551 | 1.523 | 1.523 | 1.509 | 1.495 | 1.481 | 1.467 | 1.453 | 1.439 | 1.425 | 1.411 | 1.397 | 1.383 | 1.369 | 1.355 | 1.341 | 1.327 | 1.313 | 1.299 | 1.285 | 1.271 | 1.257 | 1.243 |
| 77.92 | 1.530 | 1.516 | 1.502 | 1.488 | 1.474 | 1.460 | 1.446 | 1.432 | 1.418 | 1.404 | 1.390 | 1.376 | 1.362 | 1.348 | 1.334 | 1.320 | 1.306 | 1.292 | 1.278 | 1.264 | 1.250 | 1.236 | 1.222 | 1.208 |
| 74.38 | 1.495 | 1.481 | 1.461 | 1.453 | 1.439 | 1.425 | 1.411 | 1.397 | 1.383 | 1.369 | 1.355 | 1.341 | 1.327 | 1.313 | 1.299 | 1.285 | 1.277 | 1.257 | 1.243 | 1.229 | 1.215 | 1.201 | 1.187 | 1.173 |
| 70.84 | 1.460 | 1.446 | 1.432 | 1.418 | 1.404 | 1.390 | 1.376 | 1.362 | 1.348 | 1.334 | 1.320 | 1.306 | 1.292 | 1.278 | 1.264 | 1.250 | 1.236 | 1.222 | 1.208 | 1.194 | 1.180 | 1.166 | 1.152 | 1.138 |
| 67.30 | 1.425 | 1.411 | 1.397 | 1.383 | 1.369 | 1.355 | 1.341 | 1.327 | 1.313 | 1.299 | 1.285 | 1.271 | 1.257 | 1.243 | 1.229 | 1.215 | 1.201 | 1.187 | 1.173 | 1.159 | 1.145 | 1.131 | 1.117 | 1.103 |
| 63.76 | 1.390 | 1.376 | 1.362 | 1.348 | 1.334 | 1.320 | 1.306 | 1.292 | 1.278 | 1.264 | 1.250 | 1.236 | 1.222 | 1.208 | 1.194 | 1.180 | 1.166 | 1.152 | 1.138 | 1.124 | 1.110 | 1.096 | 1.082 | 1.068 |
| 60.22 | 1.355 | 1.341 | 1.327 | 1.313 | 1.299 | 1.285 | 1.271 | 1.257 | 1.243 | 1.229 | 1.215 | 1.201 | 1.187 | 1.173 | 1.159 | 1.145 | 1.131 | 1.117 | 1.103 | 1.089 | 1.075 | 1.061 | 1.047 | 1.033 |
| 56.68 | 1.320 | 1.306 | 1.292 | 1.278 | 1.264 | 1.250 | 1.236 | 1.222 | 1.208 | 1.194 | 1.180 | 1.166 | 1.152 | 1.138 | 1.124 | 1.110 | 1.096 | 1.082 | 1.068 | 1.054 | 1.040 | 1.026 | 1.012 | 0.998 |
| 53.14 | 1.285 | 1.271 | 1.257 | 1.243 | 1.229 | 1.215 | 1.201 | 1.187 | 1.173 | 1.159 | 1.145 | 1.131 | 1.117 | 1.103 | 1.089 | 1.075 | 1.061 | 1.047 | 1.033 | 1.019 | 1.005 | 0.991 | 0.977 | 0.963 |
| 49.60 | 1.250 | 1.236 | 1.222 | 1.208 | 1.194 | 1.180 | 1.166 | 1.152 | 1.138 | 1.124 | 1.110 | 1.096 | 1.082 | 1.068 | 1.054 | 1.040 | 1.026 | 1.012 | 0.889 | 0.984 | 0.970 | 0.956 | 0.942 | 0.928 |
| 46.06 | 1.215 | 1.201 | 1.187 | 1.173 | 1.159 | 1.145 | 1.131 | 1.117 | 1.103 | 1.089 | 1.075 | 1.061 | 1.047 | 1.033 | 1.019 | 1.005 | 0.991 | 0.977 | 0.963 | 0.949 | 0.935 | 0.921 | 0.907 | 0.893 |
| 42.52 | 1.180 | 1.166 | 1.152 | 1.138 | 1.124 | 1.110 | 1.096 | 1.082 | 1.068 | 1.054 | 1.040 | 1.026 | 1.012 | 0.998 | 0.984 | 0.970 | 0.956 | 0.942 | 0.928 | 0.914 | 0.900 | 0.886 | 0.872 | 0.858 |
| 38.98 | 1.145 | 1.131 | 1.117 | 1.103 | 1.089 | 1.075 | 1.061 | 1.047 | 1.033 | 1.019 | 1.005 | 0.991 | 0.977 | 0.963 | 0.949 | 0.935 | 0.921 | 0.907 | 0.893 | 0.879 | 0.865 | 0.851 | 0.837 | 0.823 |
| 35.44 | 1.110 | 1.096 | 1.082 | 1.068 | 1.054 | 1.040 | 1.026 | 1.012 | 0.998 | 0.984 | 0.970 | 0.956 | 0.942 | 0.928 | 0.914 | 0.900 | 0.886 | 0.872 | 0.858 | 0.844 | 0.830 | 0.816 | 0.802 | 0.788 |
| 31.90 | 1.075 | 1.061 | 1.047 | 1.033 | 1.019 | 1.005 | 0.991 | 0.977 | 0.963 | 0.949 | 0.935 | 0.921 | 0.907 | 0.893 | 0.879 | 0.865 | 0.851 | 0.837 | 0.823 | 0.809 | 0.795 | 0.781 | 0.767 | 0.753 |
| 28.36 | 1.040 | 1.026 | 1.012 | 0.998 | 0.984 | 0.970 | 0.956 | 0.942 | 0.928 | 0.914 | 0.900 | 0.886 | 0.872 | 0.858 | 0.844 | 0.830 | 0.816 | 0.802 | 0.788 | 0.774 | 0.760 | 0.746 | 0.732 | 0.718 |
| 24.82 | 1.005 | 0.991 | 0.977 | 0.963 | 0.949 | 0.935 | 0.921 | 0.907 | 0.893 | 0.879 | 0.865 | 0.851 | 0.837 | 0.823 | 0.809 | 0.780 | 0.781 | 0.767 | 0.753 | 0.739 | 0.725 | 0.711 | 0.697 | 0.683 |
| 24.28 | 0.970 | 0.956 | 0.942 | 0.928 | 0.914 | 0.900 | 0.886 | 0.872 | 0.858 | 0.844 | 0.830 | 0.816 | 0.802 | 0.788 | 0.777 | 0.760 | 0.746 | 0.732 | 0.718 | 0.704 | 0.690 | 0.676 | 0.662 | 0.648 |
| 17.74 | 0.935 | 0.921 | 0.907 | 0.893 | 0.879 | 0.865 | 0.851 | 0.837 | 0.823 | 0.809 | 0.780 | 0.781 | 0.767 | 0.753 | 0.739 | 0.725 | 0.711 | 0.697 | 0.683 | 0.669 | 0.655 | 0.641 | 0.627 | 0.613 |
| 14.20 | 0.900 | 0.886 | 0.872 | 0.858 | 0.844 | 0.830 | 0.816 | 0.802 | 0.788 | 0.774 | 0.760 | 0.746 | 0.732 | 0.718 | 0.704 | 0.690 | 0.676 | 0.662 | 0.648 | 0.634 | 0.620 | 0.606 | 0.592 | 0.578 |
| 10.66 | 0.865 | 0.851 | 0.837 | 0.823 | 0.809 | 0.795 | 0.781 | 0.767 | 0.753 | 0.709 | 0.725 | 0.711 | 0.697 | 0.683 | 0.669 | 0.655 | 0.641 | 0.627 | 0.613 | 0.599 | 0.858 | 0.571 | 0.557 | 0.543 |
| 7.12 | 0.830 | 0.816 | 0.802 | 0.779 | 0.774 | 0.760 | 0.746 | 0.732 | 0.718 | 0.704 | 0.690 | 0.676 | 0.662 | 0.648 | 0.634 | 0.620 | 0.606 | 0.592 | 0.578 | 0.564 | 0.550 | 0.536 | 0.522 | 0.508 |
| 3.58 | 0.795 | 0.781 | 0.767 | 0.753 | 0.739 | 0.725 | 0.711 | 0.697 | 0.683 | 0.669 | 0.655 | 0.641 | 0.627 | 0.613 | 0.599 | 0.585 | 0.571 | 0.557 | 0.543 | 0.529 | 0.515 | 0.501 | 0.487 | 0.473 |
| 0.04 | 0.760 | 0.746 | 0.732 | 0.718 | 0.704 | 0.690 | 0.676 | 0.662 | 0.648 | 0.634 | 0.620 | 0.606 | 0.592 | 0.578 | 0.564 | 0.550 | 0.536 | 0.522 | 0.508 | 0.494 | 0.480 | 0.466 | 0.452 | 0.438 |

EMBEDDED SYSTEM MODULE THERMAL INSTALLATION VERIFICATION

BACKGROUND

According to at least one study, high temperatures account for over half of electronic equipment failures. At excessive temperatures, electronic devices have reduced reliability, increased likelihood of permanent failure, and a high risk of undergoing undetected damage. Accordingly, methods are needed to thermally protect electronic devices and to aid in the diagnosis of temperature related failures.

Sophisticated electronic modules are often encased in carriers which are in turn mounted within a multi-module shelf configured for conduction cooling of the overall system of individual modules. Such modules are generally secured within the shelf where a lock mechanism ensures not only optimal secure attachment between the electronic module and the shelf but can also provide heat transfer from the individual module to the shelf. Without a proper connection between the lock mechanism and the shelf unit, the likelihood of overheating of the electronic module increases significantly. Providing a proper connection can, therefore, aid with maintaining longevity of the electronic module.

The subject matter claimed herein is not limited to embodiments that solve any disadvantages or that operate only in environments such as those described above. Rather, this background is only provided to illustrate one exemplary technology area where some embodiments described herein may be practiced.

BRIEF SUMMARY

One embodiment illustrated herein includes a method that may be practiced for detecting an incorrectly attached heat sink, such as is associated with a lock mechanism having heat sink components. The method includes identifying a thermal ramp rate of the electronic device while the electronic device is in operation, determining that the identified thermal ramp rate exceeds a predetermined threshold ramp rate, and transmitting a fault signal to a user interface when the identified thermal ramp rate exceeds the predetermined threshold ramp rate. In some embodiments, the predetermined threshold ramp rate is selected from a plurality of threshold ramp rates based upon an ambient or component temperature and a power consumption of the electronic device.

Another embodiment includes a system for detecting an incorrectly attached heat sink, such as is associated with a lock mechanism incorporating heat sink functionality. The system includes one or more temperature sensors secured to the electronic device, a controller unit having one or more processors and one or more computer-readable media. The computer-readable media of the controller has stored thereon instructions that are executable by the one or more processors to perform of the methods illustrated herein. The system may include additional hardware for use by or in conjunction with the electronic device for carrying out the aforementioned method, such as but not limited to a programmable memory unit, a serial communication bus, and/or a user interface component.

An additional embodiment includes a computer-readable media comprising one or more physical computer-readable storage media having stored thereon computer-executable instructions that, when executed at a processor, cause a computer system to perform the method(s) for detecting an incorrectly attached heat sink component as described herein.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims, or may be learned by the practice of the invention as set forth hereinafter.

BRIEF DESCRIPTION OF THE DRAWINGS

In order to describe the manner in which the above-recited and other advantages and features can be obtained, a more particular description of the subject matter briefly described above will be rendered by reference to specific embodiments which are illustrated in the appended drawings. Understanding that these drawings depict only typical embodiments and are not therefore to be considered to be limiting in scope, embodiments will be described and explained with additional specificity and detail through the use of the accompanying drawings in which:

FIG. 5 illustrates an exemplary table of predetermined threshold ramp rates corresponding to an incorrectly attached heat sink component;

DETAILED DESCRIPTION

Embodiments illustrated herein are directed to apparatuses, systems and methods for detecting an incorrectly attached heat sink component on an electronic device. While some embodiments described herein are directed to using customized and/or existing hardware to detect one or more incorrectly attached locking mechanisms, such as wedge locks, on an embedded system module, the systems described herein may be embodied in other specific forms to detect the improper connection of a variety of heat sink components on a variety of electronic devices.

The following discussion also refers to a method that may be performed. Although the method may be discussed in a certain order or illustrated in a flow chart as occurring in a particular order, no particular ordering is required unless specifically stated, or required because one portion of method is dependent on another portion of the method being completed prior to the one portion of the portion is performed.

Figure 1A:
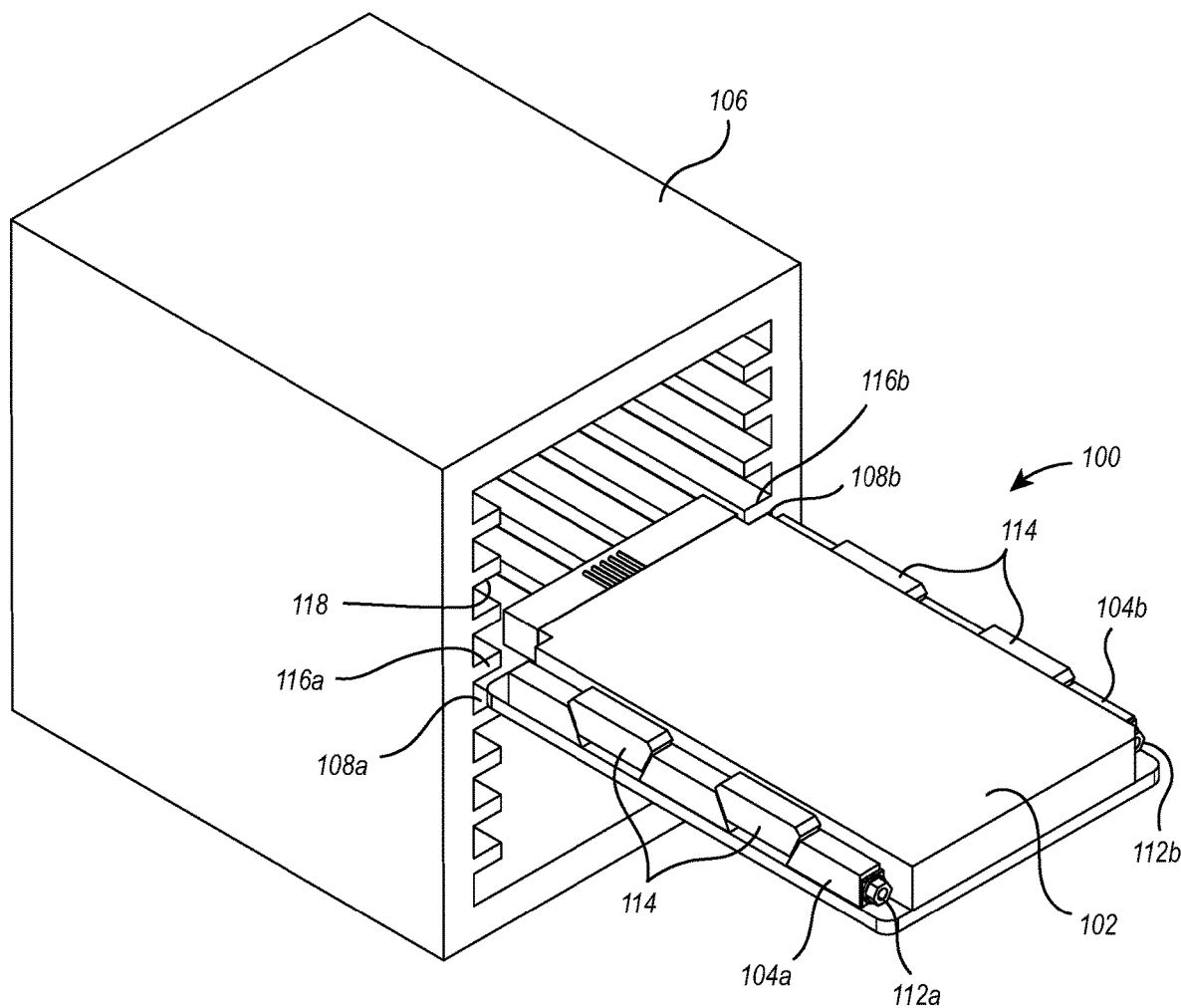
FIG. 1A illustrates an exemplary electronic device having multiple heat sink components in position for mounting within a rack.
Figure 1B:
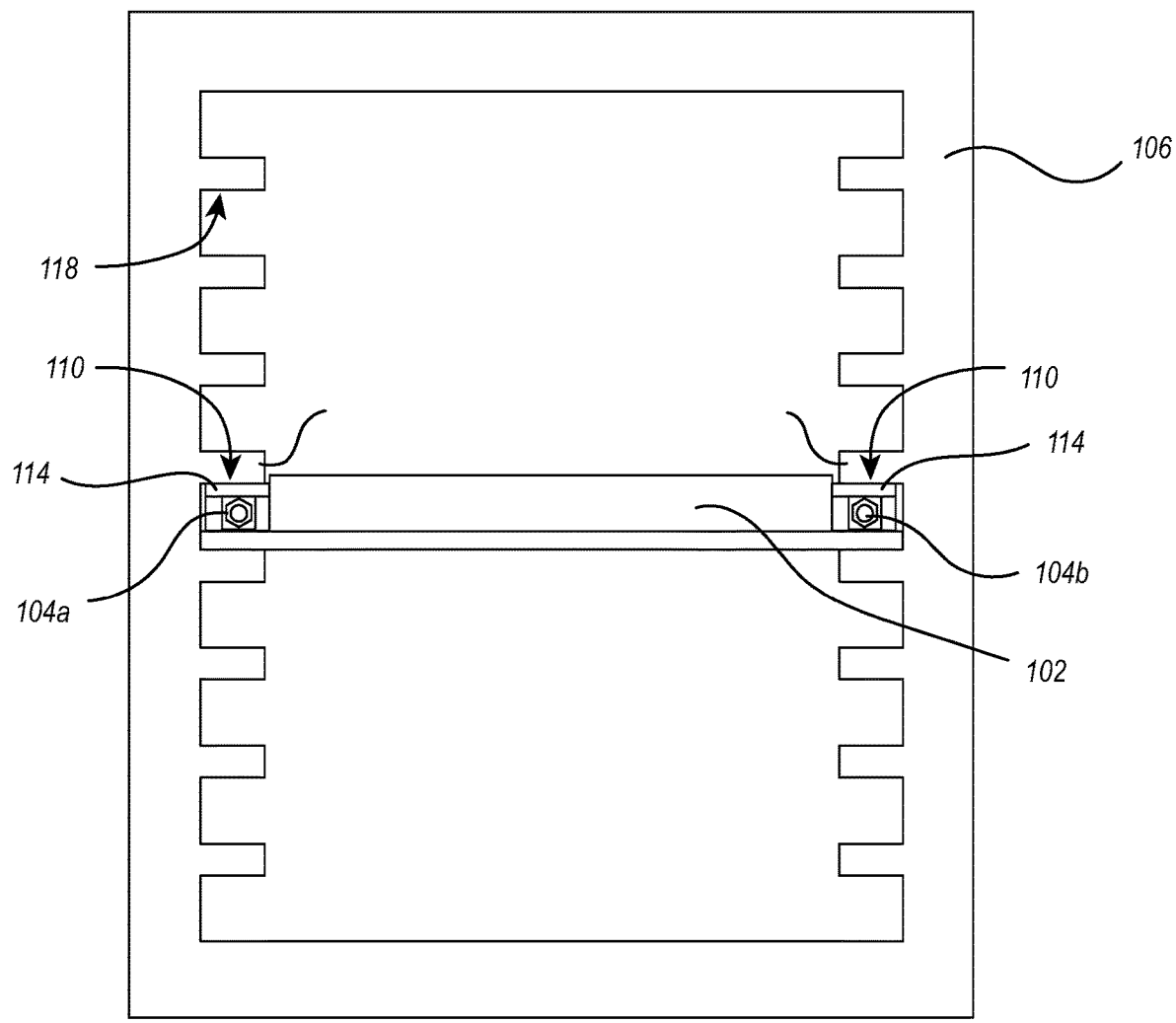
FIG. 1B illustrates the functionality of the heat sink components of the exemplary electronic device of FIG. 1A with the electronic device mounted within a rack.

Referring now to FIGS. 1A-1B, an exemplary electronic device 100 is illustrated. In the illustrated example, electronic device 100 comprises a circuit card carrier 102 and two lock mechanisms 104a, 104b for securing electronic device 100 within a circuit card rack 106 and for providing a thermal cooling path for heat removal from electronic device 100. The lock mechanisms 104a, 104, therefore, act as heat sinks to dissipate heat from the electronic device 100 to the circuit card rack 106. When lock mechanisms 104a, 104b are properly connected or engaged within respective mounting slots 108a, 108b of circuit card rack 106, a thermal cooling path 110 is established between electronic device 100 and circuit card rack 106, ensuring optimum heat dissipation during operation of electronic device 100.

One skilled in the art will appreciate that, in view of the present disclosure, electronic device 100 can include any device having heat sink components that perform optimally when properly connected or tightened to the electronic device. As a non-limiting example, electronic device 100 can be a communication module built to VITA/VPX industry standards and typically including a pair of wedge lock mechanisms for securing the device and providing a heat transfer path between the module and the chassis to which the module is secured. Other examples of electronic devices include, but are not limited to compact peripheral component interconnect (PCI) modules and any other types of conduction cooled modules incorporating wedge lock mechanisms, or any system wherein the primary thermal conduction path may become compromised or disconnected.

As illustrated, circuit card carrier 102 of electronic device 100 is configured to be inserted into mounting slots 108a, 108b of circuit card rack 106 with lock mechanisms 104a, 104b initially disengaged; the mounting slots 108a, 108b being formed between adjacent mounting supports 116a, 116b. Circuit card carrier 102 may then be secured to circuit card rack 106 by engaging lock mechanisms 104a, 104b using respective drive screws 112a, 112b. For instance, where the lock mechanisms 104a, 104b are wedge locks, rotation of the drive screws 112a, 112b causes wedges 114 to move outwardly to press against an inside surface 118 of the respective mounting slot 108a, 108b, i.e., against the mounting supports 116a, 116b. While reference herein is made to wedge locks as the lock mechanisms, 104a, 104b one skilled in the art will appreciate that the present invention can be used with other lock mechanisms that lock a circuit card carrier within mounting slots of a circuit card rack and provide a thermal cooling path for heat removal. Those lock mechanisms can include, but are not limited to, any type of module Circuit Card Assembly (CCA) locking mechanism that is used to establish a thermal path for conduction cooling.

In the event that an operator or technician neglects to properly engage lock mechanisms 104a, 104b, thermal cooling path 110 between circuit card carrier 102 and circuit card rack 106 is left at least partially unformed, which is likely to result in overheating of the electronic device during operation. Accordingly, methods, apparatuses, and systems of the present disclosure enable prevention of thermal damage or failure of electronic devices due to incorrectly attached heat sink components, such as lock mechanisms 104a, 104b, which results in insufficiency of the heat sink components to create the cooling thermal path for heat removal.

One skilled in the art will appreciate that the disclosed methods, systems and apparatuses are not to be limited to detection of incorrectly attached lock mechanisms, such as wedge locks, as illustrated. For instance, embodiments can readily be implemented to detect improper connection of virtually any type or style of heat sink component or to detect a variety of related thermal issues during operation of an electronic device.

Figure 2:
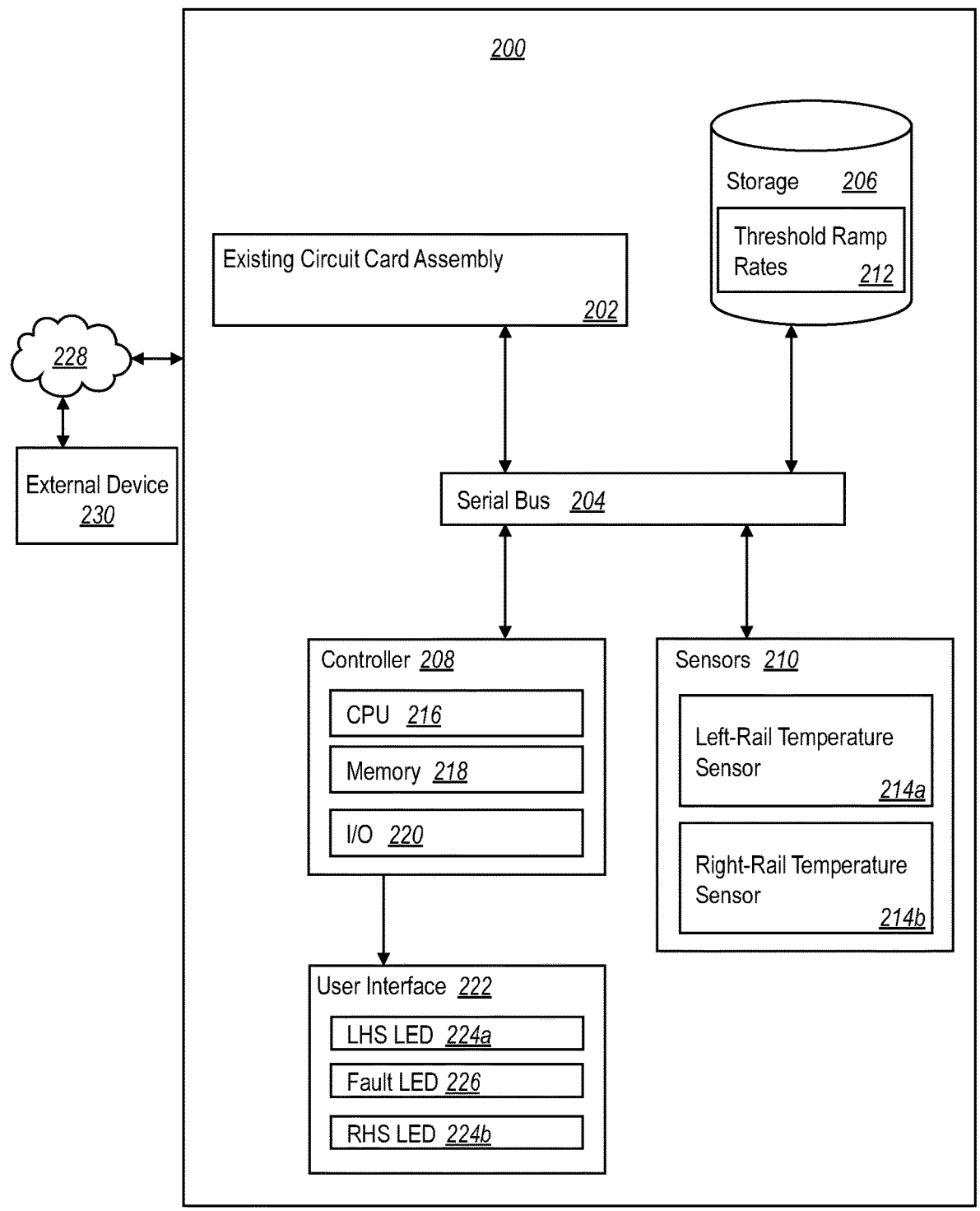
FIG. 2 illustrates an overview of a system for detecting incorrectly attached heat sink components.

Turning to FIG. 2, schematically illustrated is a system 200 for detecting an incorrectly attached heat sink component on an electronic device, such as, for example, the electronic device 100 having lock mechanisms 104a, 104b. The system 200 is configured to provide a warning to the user or technician mounting the electronic device 100 to the circuit card rack 106.

As illustrated, embodiments of system 200 for detecting an incorrectly attached heat sink component on an electronic device can include hardware and software integrated with one or more existing circuit card assemblies 202 of the electronic device 100 to monitor one or more thermal ramp rates of the electronic device 100. Alternatively, the hardware, firmware, and software necessary to implement methods of the present disclosure can be implemented separate from the electronic device, such as by introduction of an additional device or computer system configured to monitor and evaluate the thermal ramp rates of the separate electronic device.

As shown, system 200 includes various components in communication with circuit card assembly 202 via a serial bus 204. For example, serial bus 204 may include an inter-integrated circuit (12C) serial communication bus. System hardware, and associated software, in communication with serial bus 204 include storage 206 for storing predetermined threshold ramp rates 212, controller 208 for processing data and transmitting fault signals and/or reset commands, and sensors 210 for measuring the present temperature of the electronic device in one or more locations. Although system 200 as shown specifically includes left and right temperature sensors 214a and 214b corresponding to left and right heat sink components (such as lock mechanisms 104a, 104b of FIGS. 1A-1B), additional or fewer sensors can be included as required. For example, if the electronic device does not have existing sensors for ambient or component temperature and/or power consumption, system 200 can be modified to include such sensors.

A controller 208, such as a micro controller unit or other controller, further includes a central processing unit (CPU) 216, dedicated memory 218, and input/output (I/O) hardware 220 for transmitting and receiving data and commands. As shown, controller 208 communicates directly with a user interface 222 to notify the user or operator of any faults detected. According to the methods disclosed herein, controller 208 receives electronic device parameters from circuit card assembly 202 and from sensors 210 through serial bus 204 to monitor the thermal response of the electronic device, such as electronic device 100.

As shown, controller 208 is configured to receive temperature data from left temperature sensor 214a associated with a heat sink component on a left side of the electronic device (such as lock mechanism 104a), and right temperature sensor 214b associated with a heat sink component on the right side of the electronic device (such as lock mechanism 104b). System 200 is thus configured to monitor the thermal response associated with two separate heat sink components. For instance, controller 208 is configured to continuously calculate thermal ramp rates from temperature readings provided by left and right temperature sensors 214*a* and 214*b* and compare them to threshold ramp rates 212 accessed from storage 206. If, at any time during operation of system 200, the calculated thermal ramp rate exceeds the corresponding threshold ramp rate, controller 208 transmits a fault signal to user interface 222.

Specifically, if the thermal ramp rate calculated from data received from left temperature sensor 214*a* exceeds the threshold thermal ramp rate corresponding to the electronic device's present ambient or component temperature and power consumption, then controller 208 activates an LED or other indicator 224*a* to notify the operator that a heat sink component on the left side of the device is incorrectly attached. Likewise, if the thermal ramp rate calculated from data received from right temperature sensor 214*b* exceeds the threshold thermal ramp rate corresponding to the electronic device's present ambient or component temperature and power consumption, then controller 208 activates an LED or other indicator 224*b* to notify the operator that a heat sink component on the right side of the device is incorrectly attached. Also, a general fault LED 226 is included to enable indication of additional faults or errors, such as a threshold temperature is reached. Alternatively, user interface 222 can include any means for notifying the operator, such as a computer monitor, an LCD display, a speaker, and so forth.

Additionally, hardware system 200 can be configured to communicate through a network 228 with an external device 230, to allow for monitoring and adjustments to system 200 and its various components, or implementation and adjustment of software-based methods according to the present disclosure. Alternatively, external device 230 can be in direct communication with hardware system 200 via a wired or wireless connection.

Figure 3:
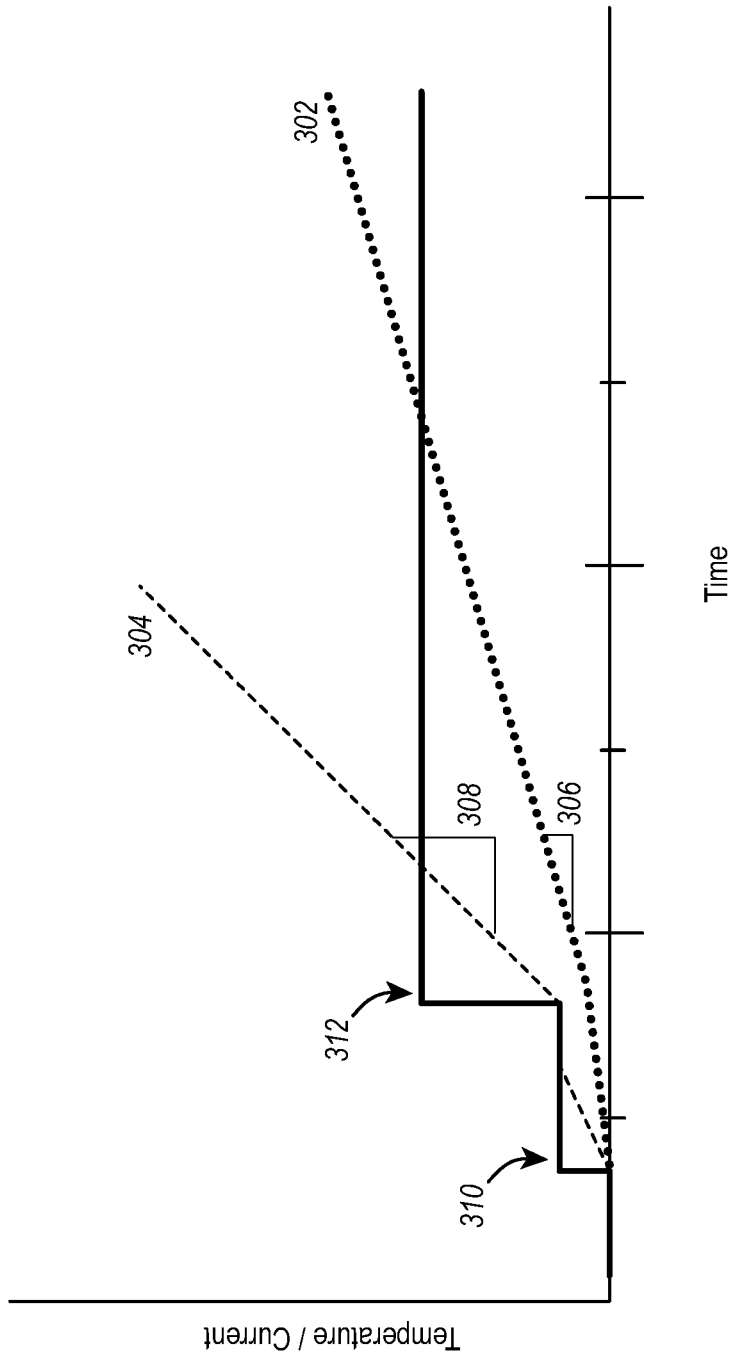
FIG. 3 illustrates a graphical representation of a method for detection of an incorrectly attached heat sink component.

Referring now to FIG. 3, a graphical representation of the temperature of the electronic device, such as electronic device 100 of FIGS. 1A-1B, in relation to time in operation. In particular, FIG. 3 illustrates a typical thermal response of the electronic device, such as electronic device 100 of FIGS. 1A-1B, under two controlled scenarios: (1) first temperature curve 302 corresponds to an electronic device having an effective thermal cooling path provided by properly connected heat sink component such as when the lock mechanisms 104*a*, 104*b* mate with the slots 108*a*, 108*b*; and (2) second temperature curve 304 corresponds to the same electronic device having an ineffective or nonexistent thermal cooling path due to an incorrectly attached heat sink component, such as when at least one of the lock mechanisms 104*a*, 104*b* ineffectively mates or engages with the mounting supports 116*a*, 116*b*.

Existing methods for preventing thermal damage and device failure due to overheating include monitoring the temperature of the electronic device and issuing a warning or shutting down the electronic device when a predetermined threshold temperature is reached. Use of an absolute thermal limit based on the temperature of the electronic device can often lead to damage to the electronic device as the warning and/or shutdown of the device is only implemented after an excessive temperature is reached or after the temperature is rising too quickly to prevent overheating. Further, selecting an absolute thermal limit corresponding to a conservatively low temperature in order to prevent thermal damage can substantially limit the utility of the electronic device.

In contrast, methods, apparatuses, and systems of the present disclosure rely on thermal ramp rate to determine whether a heat sink component, such as a wedge lock as the lock mechanism, is connected properly to produce an effective thermal cooling path. By determining a threshold thermal ramp rate upon which a fault warning and/or shutdown command is issued, embodiments of the present disclosure enable detection of incorrectly attached heat sink components earlier than the existing methods that rely on a threshold temperature of the electronic device. Absolute thermal limits can still be set to account for the various factors that may lead to overheating of the electronic device but, according to embodiments of the present disclosure, detection of incorrectly attached heat sink devices can be achieved well before an excessive temperature is reached.

As illustrated in FIG. 3, the thermal ramp rate 308 (i.e., the slope or differential with respect to time) of the second temperature curve 304 exceeds the thermal ramp rate 306 of the first temperature curve 302. In other words, the thermal ramp rate 308 experienced by the electronic device, such as electronic device 100, having an incorrectly attached heat sink component, such as lock mechanisms 104*a*, 104*b*, exceeds the thermal ramp rate 306 of the electronic device 100 having properly secured heat sink components or lock mechanisms 104*a*, 104*b*. By selecting a threshold thermal ramp rate based on thermal ramp rate 308 that electronic device 100 exhibits under controlled circumstances, methods of the present disclosure enable detection of incorrectly attached heat sink components or lock mechanisms 104*a*, 104*b* before the electronic device 100 reaches an excessive temperature.

According to embodiments of the present disclosure, the thermal ramp rate 308 is identified as a threshold ramp rate for the particular temperature and power consumption level (i.e., current) at which the thermal ramp rates 306, 308 of FIG. 3 were observed. For example, the electronic device 100 is turned on at 310 and allowed to power up until 312 is reached, upon which monitoring of the thermal ramp rate of the electronic device 100 is initiated by, for example, a monitoring system such as system 200 of FIG. 2. While monitoring the thermal ramp rate, if the rate exceeds predetermined thermal ramp rate 308 (accessible by controller 208 from storage 206), a fault signal is transmitted by controller 208 to a user interface 22 to notify the operator and, if appropriate, a reset command is issued to shut down the electronic device 100 or an existing circuit card assembly device 202 thereof.

Figure 4:
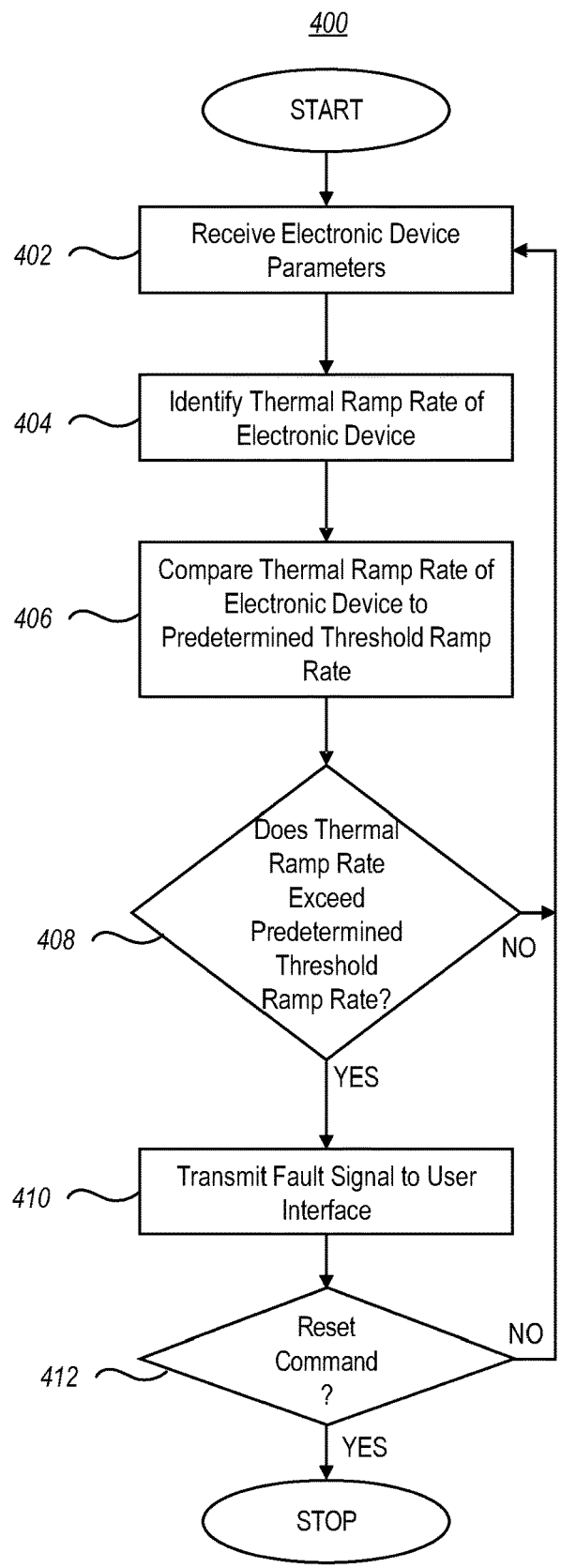
FIG. 4 illustrates a flowchart of a method for detecting an incorrectly attached heat sink component on an electronic device.

Referring now to FIG. 4, a flowchart of a method 400 for detecting an incorrectly attached heat sink component on the electronic device 100 is illustrated. Method 400 begins at 402 with receiving electronic device parameters either directly from the electronic device 100 or via sensors directly associated with the electronic device 100 (such as sensors 210). Device parameters are preferably received in real-time for continuous monitoring, and may include ambient temperature (i.e., the environmental temperature in which the electronic device is presently operating) or the temperature of the electronic device or a component thereof, power consumption (i.e., electrical current), and the temperature of the electronic device at one or more locations (e.g., left and right temperature sensors 214*a*, 214*b*).

Next, at 404, the method includes identifying a thermal ramp rate of the electronic device 100 by periodically calculating the slope of the temperature response of the thermal device at the aforementioned one or more locations. After a thermal ramp rate of the electronic device 100 has been identified, the method includes, at 406, comparing the identified thermal ramp rate to a predetermined threshold ramp rate 212, such as described in relation to FIG. 3 herein. In some embodiments, a plurality of predetermined threshold ramp rates 212 is utilized, each based on the present ambient or component temperature and/or power consumption of the electronic device, as shown in FIG. 5, for example. Embodiments may also include a single threshold ramp rate 212 that does not depend on present device parameters if appropriate under the circumstances. For example, if an electronic device 100 is intended for use in environments with generally consistent ambient temperatures and at a generally consistent level of power consumption, a plurality of predetermined threshold ramp rates may not be necessary.

If it is determined that the calculated thermal ramp rate does not exceed the predetermined ramp rate 212, such as the decision at 408 being negative, the method is returned to receiving electronic device parameters at 402 and each the method is repeated in order to continuously monitor the thermal ramp rate of the electronic device 100. During such continuous monitoring, however, if it is determined that the calculated thermal ramp exceeds the predetermined ramp rate 212 at 408, such that decision is in the affirmative, the method proceeds to transmit a fault signal to a user interface 222 to notify the operator of an incorrectly attached heat sink component or related issue, such as a 410.

Following fault signal transmission at 410, so long as the electronic device 100 remains in operation, method continues to monitor the ramp rate by receiving the electronic device parameters at 402, and determining with each repetition of method 400 whether to continue transmission of the fault signal at 410. Additionally, or alternatively, reset or shutdown commands can be transmitted to the electronic device 100, depending on the requirements set by the operator at 412. For instance, if the electronic device 100 is critical to the operation of the overall system or vital to the safety of the operator, it may be determined that the electronic device 100 should be permitted to continue operation despite any indication of incorrectly attached heat sink components. By contrast, in order to prevent damage to the electronic device 100, a non-critical electronic device 100 may be configured to automatically reset or shut down when it is determined that a heat sink component is incorrectly attached.

Referring now to FIG. 5, an exemplary table of predetermined threshold ramp rates 212 is presented. The table of FIG. 5 is illustrative and not indicative of absolute values of threshold ramp rates, with it being understood by one skilled in the art that various threshold ramp rates are possible. For instance, and not by way of limitation, threshold ramp rates may be impacted by one or more of the following: module thermal capacitance, wedge lock thermal resistance, module power dissipation and power distribution, the total power distribution of the next higher assembly, combinations and/or modifications thereof. It will be understood by one skilled in the art that the preceding is a non-exhaustive list of variables that could impact the ramp rates and that one skilled in the art can identify other variables that can impact the ramp rates based upon, at least in part, this disclosure or otherwise contemplated by this disclosure.

One or more tables such as that shown in FIG. 5 may thus be stored in a storage device 206 of a hardware system 200 according to embodiments of the present disclosure, such that controller 208 may be configured to select a predetermined ramp rate 212 from the table(s) based on parameters received from sensors 210 or directly from electronic device 100. As shown, each predetermined threshold ramp rate 212 corresponds to a particular ambient or component temperature and power consumption of the electronic device 100. Such a table of predetermined threshold ramp rates 212 may be determined on an individual basis for each electronic device 100, or parameters can be determined for basic modifications to a baseline electronic device to simplify the process. By determining threshold ramp rates 212 under various operation conditions, methods of the present disclosure enable effective detection of incorrectly attached heat sinks before the electronic device 100 reaches damaging temperatures, thus preventing thermal damage to the electronic device 100.

Figure 6:
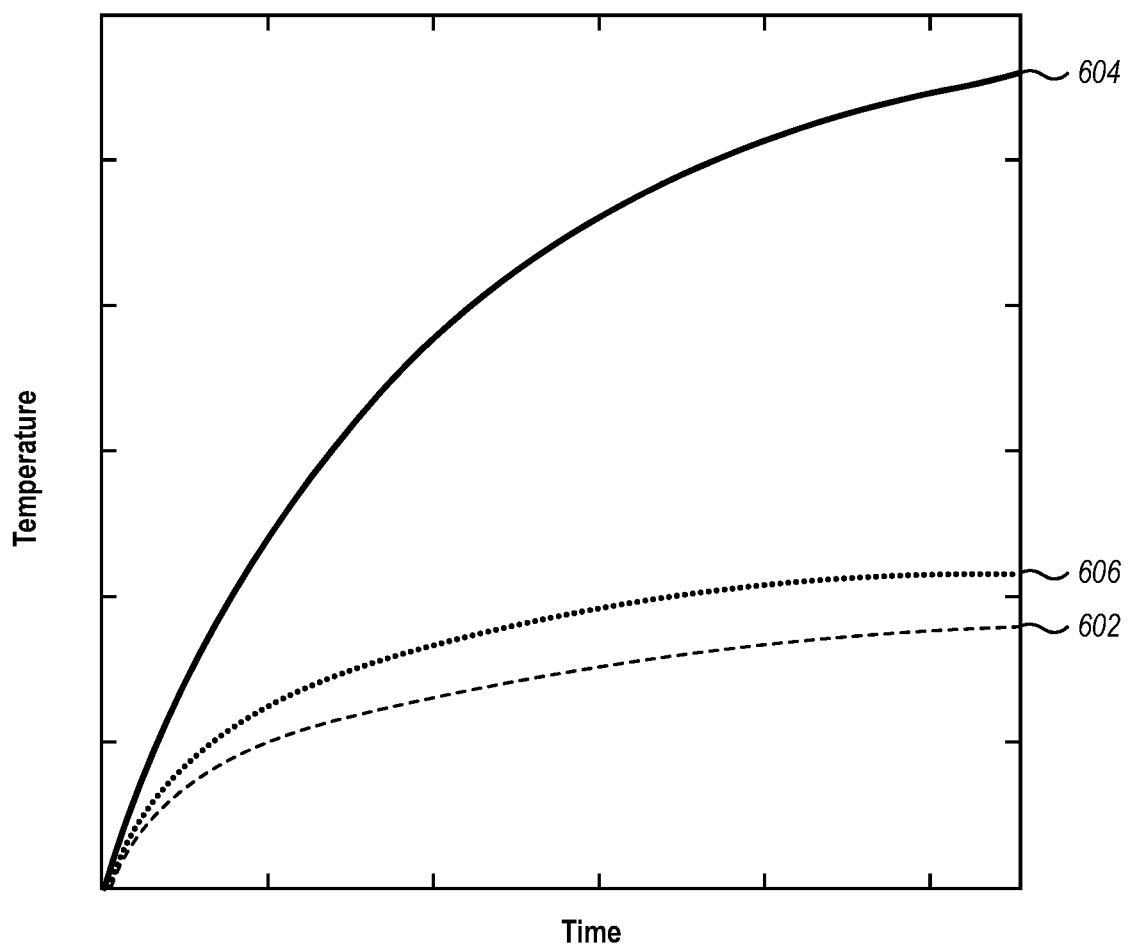
FIG. 6 illustrates a graph showing exemplary ramp rates corresponding to a varying number of both correctly and incorrectly attached heat sink components.

Referring now to FIG. 6, a graphical representation of thermal response of an electronic device 100 for varying numbers of tightened and untightened heat sink components is shown. As illustrated, curve 602 represents to a baseline thermal response on electronic device 100 having two properly connected and tightened lock mechanisms, such as wedge lock devices, curve 604 represents the thermal response of the electronic device 100 when both lock mechanisms, such as wedge locks, are completely loosened, and curve 606 represents the thermal response when one of the lock mechanisms, such as wedge locks, is tightened properly and the other is loosened.

As discussed in relation to FIG. 3, a threshold ramp rate can thus be determined from curve 604. Additionally, an offset ramp rate can be determined from curve 606. In application, the offset ramp rate can be used to indicate to an operator when one of the heat sink components is incorrectly attached while the other is properly connected. Such an indication of partial fault may enable the operator to continue operation of the electronic device cautiously to complete the intended task while monitoring the thermal response. Embodiments of the present disclosure can thus enable detection of varying numbers of incorrectly attached heat sink components. For instance, if it is determined that the thermal ramp rate of electronic device 100 exceeds the thermal ramp rate corresponding to offset curve 606 but has not reached the threshold ramp rate corresponding to curve 604, a fault signal indicates to an operator that one but not both of lock mechanisms 104a, 104b is incorrectly attached.

Figure 7:
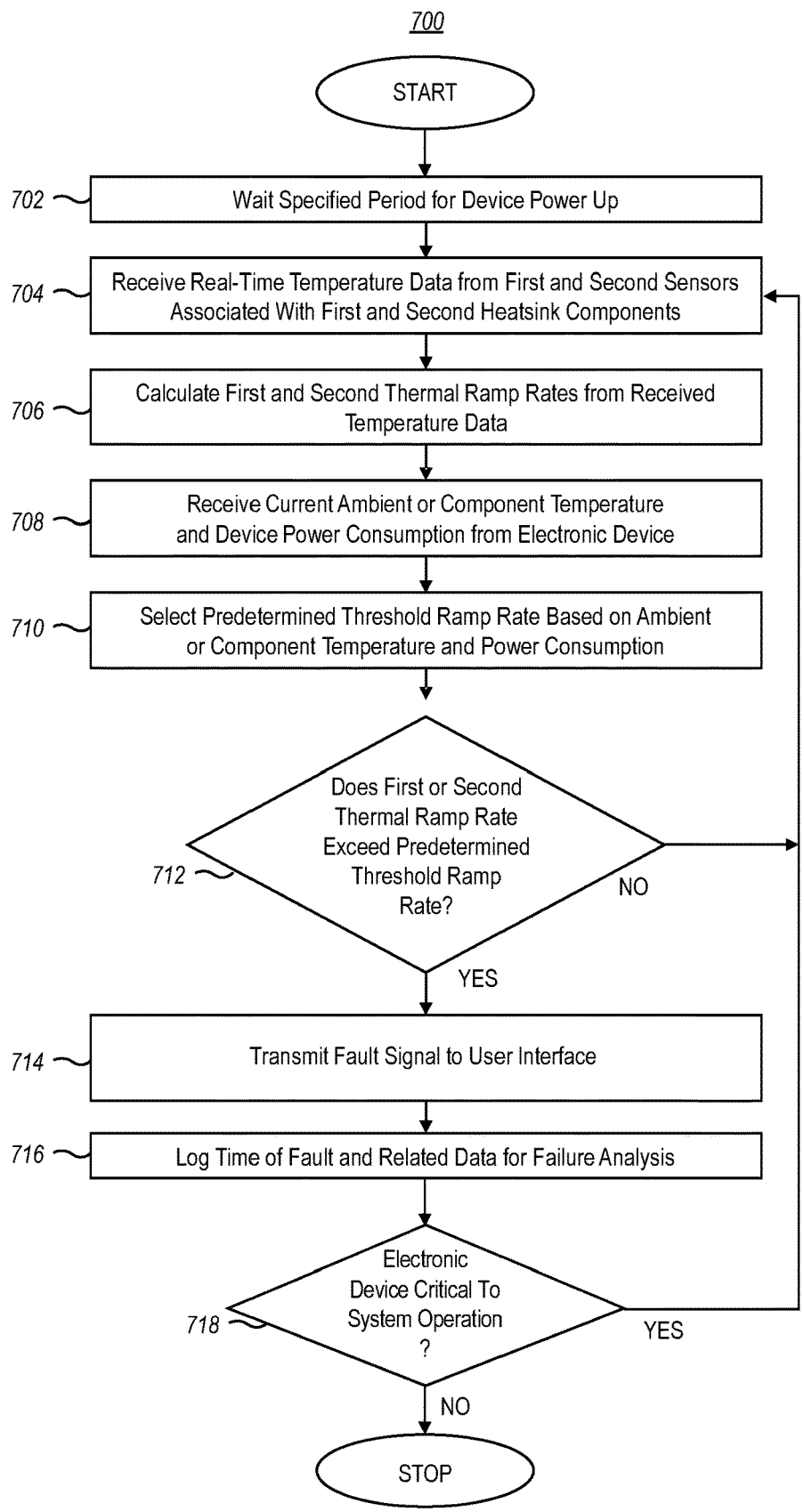
FIG. 7 illustrates a flowchart of a method for detecting an incorrectly attached heat sink component on an electronic device having at least two separate heat sink components.

Referring now to FIG. 7, a flowchart of a method 700 for detecting an incorrectly attached heat sink component on an electronic device 100 is illustrated. In particular, method 700 enables individual detection of at least two separate heat sink components, such as opposing lock mechanisms 104a, 104b, such as wedge locks, on a circuit card carrier 102, as shown in FIGS. 1A-1B. One skilled in the art should appreciated that method 700 can be reduced or expanded to monitor fewer or additional heat sink components if so desired.

Method 700 begins at 702 with waiting a specified period of time to allow the electronic device to power up before beginning to monitor for incorrectly attached heat sink components. Monitoring of the thermal response before the device is powered up could result in premature fault signals as the thermal ramp rate is generally greater during power up (as shown in FIG. 3, for example) and could thus exceed the predetermined thermal ramp rate temporarily.

After the specified period has passed, the method at 704 includes the receipt of real-time temperature data from first and second sensors (e.g., left and right temperature sensors 214a, 214b) associated with first and second heat sink components 104a, 104b. In other words, the first sensor 214a is placed in relative proximity to the first heat sink component 104a, and the second sensor 214b is placed in relative proximity to the second heat sink component 104b.

The method utilizes the received real-time temperature data from the first and second sensors 214a, 214b to calculate respective first and second thermal ramp rates at 706.

The current ambient or component temperature and power consumption of the device are received from sensors 210 associated with the electronic device 100 at 708. These two parameters are then used to select a predetermined threshold ramp rate 212 from a chart or database 206 of threshold ramp rates 212, the selection based on the current ambient or component temperature and power consumption of the electronic device 100 at 710. An example chart of threshold ramp rates 212 corresponding to ambient or component temperature and power consumption is provided in FIG. 5 of the present disclosure.

The selected threshold ramp rate 212 is compared to the calculated first and second thermal ramp rates at 712, and if it is determined that either the first thermal ramp rate or the second thermal ramp rates does not exceed the predetermined ramp rate 212 corresponding to the present ambient or component temperature and power consumption (updated at each iteration of the method at 710), real-time temperature data is received, at 704, and the thermal ramp rate associated with the first and second heat sink components 104a, 104b is continuously monitored (repeating the method from 704 through 712). During such continuous monitoring, however, if it is determined that the calculated first or second thermal ramp exceeds the predetermined ramp rate 212, such as at 712, a fault signal is transmitted to a user interface 222 to notify the operator of an incorrectly attached heat sink component 104a or 104b, or related issue at 714. The fault signal can generally indicate a fault or can specify which of the heat sink components 104a or 104b is incorrectly attached.

Various fault signals can be transmitted for various scenarios. For instance, if it is determined that the first thermal ramp rate exceeds the second thermal ramp rate by a specified amount, the operator is notified that the first heat sink component 104a is incorrectly attached or otherwise at fault. Stated another way, if the first thermal ramp rate is greater than the second thermal ramp rate, the transmitted fault signal identifies that the heat sink component 104a is incorrectly attached. If instead it is determined that the second thermal ramp rate exceeds the first thermal ramp rate, the operator is notified that the second heat sink 104b is incorrectly attached or otherwise at fault. Stated another way, if the second thermal ramp rate is greater than the first thermal ramp rate, the transmitted fault signal identifies that the heat sink component 104b is incorrectly attached. A general fault signal may also be transmitted to notify the user if either or both of the first and second thermal ramp rates exceed the threshold ramp rate 212.

When a fault signal is transmitted, a record of the fault is made at 716. The record or log can include the time the fault occurred and any related data that may be useful in subsequent failure analysis. For example, a data log is kept to inform the operator of exactly how much time passed wherein the electronic device 100 was exceeding the threshold ramp rate 212. Such a log can be stored, for example in the memory 218 of controller 208 or be written to existing storage of electronic device 100 or a separate storage device by I/O 220 of controller 208.

Finally, the method includes, at 718, a decision as to whether to continue operation of the electronic device despite an indication of an incorrectly attached heat sink component. For example, if the electronic device 100 is critical to the operation of the overall system or vital to the safety of the operator, the method includes returning to 704 to receive real-time temperature data from the first and second sensors and the method continue. By contrast, in order to prevent damage to the electronic device 100, a non-critical electronic device 100 may be configured to automatically reset or shut down when it is determined that a heat sink component is incorrectly attached, such as when the determination at 718 is in the negative. Such decisions can be predetermined and implemented automatically via software, firmware, or the like to stop or continue operation and monitoring of the electronic device.

The methods described herein may be implemented under a variety of circumstances, such as a laboratory testing of an electronic device, during inspections of a manufactured product prior to release, during an operation pre-check, during operation, and so forth.

Further, the methods may be practiced by a computer system including one or more processors and computer-readable media such as computer memory. In particular, the computer memory may store computer-executable instructions that when executed by one or more processors cause various functions to be performed, such as the acts recited in the embodiments.

Embodiments of the present invention may comprise or utilize a special purpose or general-purpose computer including computer hardware, as discussed in greater detail below. Embodiments within the scope of the present invention also include physical and other computer-readable media for carrying or storing computer-executable instructions and/or data structures. Such computer-readable media can be any available media that can be accessed by a general purpose or special purpose computer system. Computer-readable media that store computer-executable instructions are physical storage media. Computer-readable media that carry computer-executable instructions are transmission media. Thus, by way of example, and not limitation, embodiments of the invention can comprise at least two distinctly different kinds of computer-readable media: physical computer-readable storage media and transmission computer-readable media.

Physical computer-readable storage media includes RAM, ROM, EEPROM, CD-ROM or other optical disk storage (such as CDs, DVDs, etc.), magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmission media can include a network and/or data links which can be used to carry desired program code means in the form of computer-executable instructions or data structures and which can be accessed by a general purpose or special purpose computer. Combinations of the above are also included within the scope of computer-readable media.

Further, upon reaching various computer system components, program code means in the form of computer-executable instructions or data structures can be transferred automatically from transmission computer-readable media to physical computer-readable storage media (or vice versa). For example, computer-executable instructions or data structures received over a network or data link can be buffered in RAM within a network interface module (e.g., a "NIC"), and then eventually transferred to computer system RAM and/or to less volatile computer-readable physical storage media at a computer system. Thus, computer-readable physical storage media can be included in computer system components that also (or even primarily) utilize transmission media.

Computer-executable instructions comprise, for example, instructions and data which cause a general-purpose computer, special purpose computer, or special purpose processing device to perform a certain function or group of functions. The computer-executable instructions may be, for example, binaries, intermediate format instructions such as assembly language, or even source code. Although the subject matter has been described in language specific to structural features and/or the methods, it is to be understood that the subject matter defined in the appended claims is not necessarily limited to the described features or method described above. Rather, the described features and method are disclosed as example forms of implementing the claims.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, and the like. The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Alternatively, or in addition, the functionality described herein can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A system for detecting an incorrectly attached heat sink component on an electronic device, the system comprising:
    one or more temperature sensors secured to the electronic device; and
    a controller unit comprising one or more processors and one or more computer-readable media, the one or more computer-readable media of the controller unit having stored thereon instructions that are executable by the one or more processors to perform at least the following:
        receive temperature data from the one or more temperature sensors;
        calculate a thermal ramp rate of the electronic device;
        determine that the calculated thermal ramp rate exceeds a predetermined threshold ramp rate; and
        shut down the electronic device when the calculated thermal ramp rate exceeds the predetermined threshold ramp rate.

2. The system of claim 1, wherein the executable instructions are executable by the one or more processors of the controller unit to:
    receive ambient or component temperature data and power output data from the electronic device; and
    select the predetermined threshold ramp rate from a database containing a plurality of threshold ramp rates, each threshold ramp rate corresponding to a particular ambient or component temperature and power output of the electronic device.

3. The system of claim 2, further comprising a programmable memory unit having stored thereon the database containing the plurality of threshold ramp rates.

4. The system of claim 3, further comprising a serial communication bus configured to transfer data between the electronic device, the one or more temperature sensors, the programmable memory unit, and the controller unit.

5. The system of claim 4, wherein one or more components of the system are directly integrated with an existing circuit card assembly of the electronic device.

6. The system of claim 1, wherein each of the one or more temperature sensors is configured to measure a temperature of the electronic device at a location proximate a heat sink component associated therewith.

7. The system of claim 6, wherein the one or more temperature sensors comprise first and second temperature sensors, and wherein the executable instructions are executable by the one or more processors of the controller unit to:
    calculate first and second thermal ramp rates corresponding to the first and second temperature sensors respectively;
    determine that the first thermal ramp rate is greater than the second thermal ramp rate; and
    transmit a fault signal to a user interface component when the first thermal ramp rate is greater than the second thermal ramp rate, such that the user interface component indicates that the heat sink component associated with the first temperature sensor is incorrectly attached.

8. The system of claim 6, wherein the executable instructions are executable by the one or more processors of the controller unit to:
    calculate first and second thermal ramp rates corresponding to the first and second temperature sensors respectively, and
    determine that one of the first thermal ramp rate and the second thermal ramp rate is greater than the predetermined threshold ramp rate using ambient or component temperature and power output values; and
    transmit a fault signal to a user interface component when the first thermal ramp rate or the second thermal ramp rate is greater than the predetermined threshold ramp rate, such that the user interface component indicates that the heat sink component associated with the first temperature sensor is incorrectly attached.

9. The system of claim 1, wherein the executable instructions are executable by the one or more processors of the controller unit to transmit a reset command to the electronic device when the calculated thermal ramp rate exceeds the predetermined threshold ramp rate.

10. The system of claim 1, wherein the electronic device comprises at least one circuit card assembly enclosed within a ruggedized carrier by one or more lock mechanisms, each lock mechanism providing a thermal cooling path between the at least one circuit card assembly and the ruggedized carrier when the lock mechanism is properly secured.

11. A method of detecting an incorrectly attached heat sink component on an electronic device, the method comprising:
   identifying a thermal ramp rate of the electronic device while the electronic device is in operation;
   determining that the identified thermal ramp rate exceeds a predetermined threshold ramp rate; and
   shutting down the electronic device when the identified ramp rate exceeds the predetermined threshold ramp rate.

12. The method of claim 11, further comprising waiting a predetermined period of time to allow the electronic device to power up before identifying the thermal ramp rate of the electronic device.

13. The method of claim 11, further comprising:
   identifying an ambient or component temperature and a power consumption of the electronic device; and
   selecting the predetermined threshold ramp rate from a plurality of threshold ramp rates, each of the plurality of threshold ramp rates corresponding to a particular ambient or component temperature and power consumption of the electronic device.

14. The method of claim 11, further comprising transmitting a reset command to the electronic device when the identified thermal ramp rate exceeds the predetermined threshold ramp rate.

15. The method of claim 14, wherein transmission of the reset command is based upon an operational status of the electronic device.

16. The method of claim 11, further comprising determining that a specific quantity of heat sink components are incorrectly attached by determining that the identified thermal ramp rate exceeds a baseline ramp rate by a predetermined offset value.

17. The method of claim 11, further comprising recording a data log for analysis of the electronic device, the data log comprising a record of operational use of the electronic device whilst a heat sink component was incorrectly attached.

18. A computer-readable media comprising one or more physical computer-readable storage media having stored thereon computer-executable instructions that, when executed at a processor, cause a computer system to perform a method for detecting an incorrectly attached heat sink component on an electronic device, the method comprising:
   receiving data related to a status of the electronic device while in operation, the received data comprising a temperature of the electronic device;
   identifying a thermal ramp rate of the electronic device using the received data;
   determining that the identified thermal ramp rate exceeds a predetermined threshold ramp rate; and
   shutting down the electronic device when the identified thermal ramp rate exceeds the predetermined threshold ramp rate.

19. The computer-readable media of claim 18, wherein the received data further comprises an ambient or component temperature and a power consumption of the electronic device.

20. The computer-readable media of claim 19, wherein the method further comprises selecting the predetermined threshold ramp rate from a plurality of threshold ramp rates, each of the plurality of threshold ramp rates corresponding to a particular ambient or component temperature and power consumption of the electronic device.

* * * * *